US006555546B2

(12) United States Patent
Megens

(10) Patent No.: US 6,555,546 B2
(45) Date of Patent: Apr. 29, 2003

(54) USE OF $5HT_3$ ANTAGONISTS FOR PROMOTING INTESTINAL LAVAGE

(75) Inventor: Antonius A. H. P. Megens, Beerse (BE)

(73) Assignee: Janssen Pharmaceutics, N.V. (BE)

( * ) Notice: Subject to any disclaimer, the term of this patent is extended or adjusted under 35 U.S.C. 154(b) by 0 days.

(21) Appl. No.: 09/801,978

(22) Filed: Mar. 8, 2001

(65) Prior Publication Data

US 2001/0020025 A1 Sep. 6, 2001

Related U.S. Application Data

(62) Division of application No. 09/403,248, filed as application No. PCT/EP98/02356 on Apr. 14, 1998, now Pat. No. 6,235,745.

(30) Foreign Application Priority Data

Apr. 18, 1997 (EP) .......................................... 97201149

(51) Int. Cl.[7] ...................... A61K 31/44; A61K 31/415; A61K 31/505

(52) U.S. Cl. ....................... 514/272; 514/275; 514/304; 514/305; 514/397; 514/892

(58) Field of Search ................................ 514/272, 275, 514/304, 305, 397, 892

(56) References Cited

U.S. PATENT DOCUMENTS 5,166,145 A 11/1992 Jao et al.
5,576,317 A * 11/1996 Gonsalves ............... 514/231.2
6,103,734 A 8/2000 Ibanez ........................ 514/282

FOREIGN PATENT DOCUMENTS

| GB | 893 267 | 4/1962 | |
|---|---|---|---|
| WO | WO94/12494 | 6/1994 | ......... C07D/405/14 |
| WO | WO96/14071 | 5/1996 | ......... A61K/31/485 |

OTHER PUBLICATIONS

"Martindale The Extra Pharmacopoeia" $29^{th}$ Ed. 1989; XP002040773; p. 1073, right–hand column—p. 1074, left–hand column—p. 1129, right–hand column—p. 1130.

"Remington's Pharmaceutical Sciences" $18^{th}$ Ed. 1990; XP002040774; p. 783, left–hand column—p. 784, left–hand column—p. 786 left–hand column—p. 788.

Aliment. Pharmacol. Therap. (1990) 4, 139–144; "Colonic transit in man is slowed by ondansetron (GR38032F), a selective 5–hydroxytryptamine receptor (type 3) antagonist"; S. Gore et al.; and Abstract of same (XP002040775).

Eur. J. Cancer (1990, vol. 26, Suppl 1, pp. S12–S15); "The Clinical Pharmacology of Granisetron (BRL 43694), A Novel specific 5–$HT_3$ Antagonist"; J. Upward et al.; and Abstract of same (XP002040776).

Br. J. Pharmacol. (1994), 113 (A), 143–50; "Characterization of the 5–hydroxytryptamine receptor type involved in inhibition of spontaneous activity of human isolated colonic circular muscle"; F. Tam et al; and Abstract of same (XP002040777).

* cited by examiner

*Primary Examiner*—Frederick Krass

(57) ABSTRACT

The present invention is concerned with the use of $5HT_3$ antagonists for promoting intestinal lavage, especially in combination with an osmotic agent.

4 Claims, No Drawings

USE OF $5HT_3$ ANTAGONISTS FOR PROMOTING INTESTINAL LAVAGE

CROSS-REFERENCE TO RELATED APPLICATIONS

This application is a divisional application of Ser. No. 09/403,248, filed on Oct. 15, 1999, now U.S. Pat. No. 6,235,745 which application is the national stage of Application No. PCT/EP98/02356, filed on Apr. 14, 1998, which application claims priority from EP 97.201.149.8 filed on Apr. 18, 1997.

The present invention is concerned with the use of $5HT_3$ antagonists for accelerating intestinal lavage in combination with a laxative, in particular an osmotic agent. The present invention is also concerned with the use of said $5HT_3$ antagonists in combination with a laxative for the treatment of constipation.

Intestinal Lavage

Adequate colon preparation before diagnostic, therapeutic or surgical procedures is important because safety and diagnostic accuracy depend on adequate cleansing of the intestines. Magnesium sulfate ($MgSO_4$) or, more recently, polyethylene glycol (PEG)-electrolyte solutions (e.g., KleanPrep® or GoLytely®) have been widely used as lavage solution for colon preparation. These solutions, generally well tolerated by patients, are extremely effective in cleansing the colonic mucosa of faeculent debris. However, fairly large volumes (4 liters) and relatively long preparation times (up to 24 hours) are required. Reduction of the volume to be ingested and shortening of the preparation time would highly increase patient acceptance and comfort.

These agents may also be used to help eliminate parasites following appropriate therapy, for instance these can be used after or in combination with anthelmintics. These osmotic agents may also be used to help eliminate toxic material in some cases of poisoning.

$5HT_3$ Antagonists $5HT_3$ receptors appear to mediate the excitatory actions of 5-HT (serotonin) in the peripheral nervous system. The peripheral $5HT_3$ receptor plays a pivotal role in the process of emesis induced by cytotoxic chemotherapy and radiotherapy. Peripheral $5HT_3$ antagonists are also being studied for the treatment of irritable bowel syndrome and visceral pain. Evidence has accumulated showing the presence of $5HT_3$ receptors in the central nervous system. Central $5HT_3$ receptors have been implicated in cognition and memory disorders, anxiety and dopamine modulation of the mesolimbic structures. Antagonists of the $5HT_3$ receptor have been proposed for treating these disorders. In animal models of anxiety, $5HT_3$ receptor antagonists have been shown to exert anxiolytic properties similar to those of benzodiazepines but without sedative, anticonvulsant and muscle relaxant actions. Ondansetron hydrochloride, launched in 1990 as an antiemetic, is being studied in clinical trials for the treatment of age-related cognition disorders and generalized anxiety. Recent studies have suggested an interrelation between the serotonergic and dopaminergic systems, especially through the $5HT_3$ receptor. $5HT_3$ antagonists may thus have potential as therapeutic agents for the treatment of hyperdopaminergic disease states such as schizophrenia, without presenting the side effects liability generally associated with classic neuroleptics. (Joseph R. Prous, "*The Year's Drug News, Therapeutic Targets,* 1994 *Edition=l* )

5-$HT_3$-receptor antagonists can be identified by the fact that they are active, for example, in antagonising the Von Bezold-Jarisch chemoreflex evoked by serotonin in rats (*Pharmacology and Toxicology,* 70, *Supp II,* 17–22 (1992)).

It is known that $5HT_3$ receptor antagonists slow colonic transit and may even cause mild constipation. (*Aliment. Pharmacol. Therap.* (1990), 4, 139–144; *Digestive Diseases and Sciences, vol* 35, 4, 477–480). Hence it was quite surprising to find that $5HT_3$ antagonists have a synergistic effect with osmotic agents to obtain intestinal lavage, i.e. an induced form of diarrhea which is quite the opposite of constipation.

Interesting $5HT_3$ antagonists are Azasetron HCl, Granisetron HCl, Ondansetron HCl, Tropisetron, DAT-582, Dolasetron mesylate, Itasetron, N-3389, Pancopride, Ramosetron HCl, RG-12915, (R)-Zacopride, Lurosetron, E-3620, GK-128, KB-6933, KF-20170, and SL-90.0539.

An equally interesting $5HT_3$ antagonist is (−)-cis-4-amino-5-chloro-2,3-dihydro-N-[1-[3-[(3,4-dihydro-4-oxo-2-pyrimidinyl)amino]propyl]-3-methoxy-4-piperidinyl]-2,2-dimethyl-7-benzofurancarboxamide, which will be referred to hereinafter as "COMPOUND A", which is described as compound number 1 of WO 94/12494, published Jun. 9, 1994.

Of course the pharmaceutically acceptable acid or base addition salt of the $5HT_3$ antagonists are also intended to be included in the present invention. The pharmaceutically acceptable acid addition salts as mentioned hereinabove are meant to comprise the therapeutically active non-toxic acid addition salt forms which the $5HT_3$ antagonists are able to form. The latter can conveniently be obtained by treating the base form with such appropriate acid. Appropriate acids comprise. for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The $5HT_3$ antagonists containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Laxatives

Laxatives are drugs that promote defecation. Precise mechanisms of action of many laxatives remain uncertain because of the complex factors that affect colonic function, prominent variations of water and electrolyte transport among experimental species and preparations, and a certain costiveness of research in this area. Three general mechanisms of laxative action can be described. (1) By their hydrophilic or osmotic properties, laxatives may cause retention of fluid in colonic contents, thereby increasing bulk and softness and facilitating transit. (2) Laxatives may act, both directly and indirectly, on the colonic mucosa to decrease net absorption of water and NaCl. (3) Laxatives may increase intestinal motility, causing decreased absorption of salt and water secondary to decreased transit time. Mostly one recognizes three major classes of laxatives, i.e.

1) dietary fiber and bulk-forming laxatives, 2) saline and osmotic laxatives and 3) stimulant laxatives. (see *Goodman and Gilman, seventh edition, pp* 994 to 1003).

The bulk-forming laxatives include a wide range of natural and semisynthetic polysaccharides and cellular derivatives that are only partially digested. The undigested portions are hydrophilic and swell in the presence of water to form a viscous solution or gel. The increased intraluminal pressure reflexively stimulates peristalsis, diminishes colonic transit time and produces a soft gelatinous stool (*"Remington's Pharmaceutical Sciences",* page 783–786, 1990, Mack Publishing Company, Easton, Pa., 18th edition).

The stimulant laxatives act on the intestinal tract to increase its motor activity. The more commonly employed agents are the anthraquinone laxatives, such as, e.g. cascara sagrada and senna; the diphenylmethane derivatives, such as, e.g. phenolphtalein and bisacodyl; and castor oil (*"Remington's Pharmaceutical Sciences",* page 783–786, 1990, Mack Publishing Company, Easton, Pa., 18th edition).

Saline and osmotic laxatives are the primary class of laxatives envisaged in this invention.

Saline and osmotic laxatives include various magnesium salts; the sulfate, phosphate, and tartrate salts of sodium and potassium; the dissacharide lactulose; glycerin; and sorbitol. They are poorly and slowly absorbed and act by their osmotic properties in the luminal fluid.

Two examples of these osmotic agents which are commercially available for intestinal cleansing are KleanPrep® and GoLytely®.

The present invention is concerned with the use of a $5HT_3$ antagonist for the manufacture of a medicament that will improve, accelerate or promote the intestinal cleansing by laxatives, in particular osmotic agents. Hence, a method of treatment is claimed whereby an effective amount of a $5HT_3$ antagonist is administered to a warmblooded animal, in particular a mammal, in combination with a laxative, in particular an osmotic agent.

The terms "accelerating", "improving", or "promoting" are used as synonyms throughout this text.

The patients envisaged in this treatment are people whose bowel needs to be cleaned prior to diagnostic or surgical procedures. Another group of patients are those patients who are to be prevented from straining at the stool, these patients include people suffering from hernia or cardiovascular disease. In addition, the combination of the present invention can be indicated, both before and after surgery, to maintain soft feces in patients with hemorrhoids and other anorectal disorders.

Osmotic agents at cathartic doses are frequently employed prior to radiological examination of the gastrointestinal tract, kidneys, or other abdominal or retroperitoneal structures and prior to elective bowel surgery. Hence, also for these applications the presently described combination may be useful.

Furthermore the combination of the present invention can also be used in the treatment of drug overdosage and poisoning, by removing agents from the intestine. The combination of the present invention may also be employed in further combination with with certain anthelmintics.

As is demonstrated in the experimental part the present invention provides a method to accelerate and/or enforce the action of laxatives, especially osmotic agents. The laxatives can be administered or co-administered orally or rectally. Also provided is a method of accelerating intestinal lavage in a warm-blooded animal, in particular a mammal, by administration of a laxative in combination with an effective amount of a $5HT_3$-antagonist.

In general, "co-administration" means that the laxative and the $5HT_3$-antagonist are present in the gastrointestinal tract during at least partially overlapping times. Additionally, "co-administration" comprehends administering more than one dose of said laxative within 1 hour after a dose of the $5HT_3$-antagonist, in other words, the $5HT_3$-antagonist need not be administered again before or with every administration of said laxative, but may be administered intermittently during the course of treatment.

The present invention is also concerned with the use of said $5HT_3$ antagonists in combination with a laxative for the treatment of constipation, such as acute constipation, chronic constipation or refractory constipation. Consequently, a method is provided to treat constipation, such as, e.g. acute constipation, chronic constipation or refractory constipation, in warm-blooded animals, in particular mammals, by administration of a laxative in combination with an effective amount of a $5HT_3$ antagonist.

The $5HT_3$-antagonists may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier. Said carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of the compounds of formula (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The dosages of the drugs used in the present invention must, in the final analysis, be set by the physician in charge of the case, using knowledge of the drugs, the properties of the drugs in combination as determined in clinical trials, and the characteristics of the patient, including diseases other than that for which the physician is treating the patient.

In general it is contemplated that an effective amount of a $5HT_3$ antagonist would be from about 0.001 mg/kg to about 50 mg/kg body weight, preferably from about 0.02 mg/kg to about 5 mg/kg body weight. A method of treatment may also include administering the active ingredient on a regimen of between two or four intakes per day.

As an additional feature of the invention, this invention provides a therapeutic package suitable for commercial sale, comprising a container, an dosage form of a $5HT_3$ antagonist and a laxative, in particular an osmotic agent. This laxative or osmotic agent is often in the form of a powder, which is normally to be dissolved or suspended in a certain amount of water. Consequently, the present invention also relates to a product comprising a $5HT_3$ antagonist and a laxative, in particular an osmotic agent, for simultaneous, separate or sequential use in the treatment of constipation or for promoting intestinal lavage, provided that said product does not contain an opioid antagonist. Such a product may comprise a kit comprising a container containing a pharmaceutical composition of a laxative, and another container comprising a pharmaceutical composition of the $5HT_3$ antagonist. The product with separate compositions of the laxative and the $5HT_3$ antagonist has the advantage that appropriate amounts of each component, and timing and sequence of administration can be selected in function of the patient.

The proviso is intended to exclude the combinations as disclosed in WO-96/14071. WO-96/14071, published on May 17, 1996, discloses combinations consisting of laxatives, α-adrenergic agents, antiemetic agents, gastric protectors, optionally proton pump inhibitors, anxiolytic compounds, an anesthetic sleep-inducing agent, and an opioid antagonist, such as nalaxone or naltrexone; intended to suppress dependence on opioids.

Experimental Part

Beagle dogs of both sexes and varying in body weight were used. During the experiments, the dogs were individually housed in cages. They were uniquely identified by an ear tattoo number (received at the time of weaning). The animals were fasted overnight but were given free access to fresh tap water via automatic drinking nipples in the back of the cage.

Binding Affinity for the $5HT_3$ Receptor

In vitro $5HT_3$ receptor binding was measured using N×G 108CC15 cells and $[^3H]$GR 65630. Cells were homogenized in tris.HCl buffer (20 mM, pH=7.5) containing NaCl (154 mM); the final cell concentration corresponded to approximately $10^6$ cell/ml. Incubation mixtures for radioligand binding assays were composed of 0.5 ml membrane suspensions, 0.025 ml $[^3H]$GR 65630 (final concentration 2 nM), and 0.025 ml either solvent (10% dimethylsulfoxide) for total binding, or tropisetron (final concentration 1.0 $\mu$M) for non-specific binding, or drug solution. The incubation was run for 60 minutes at 37° C. Labelled membranes were collected and raised by rapid filtration under suction over Walkman GF/B plan fibre filters (presoaked in 0.1% polyethyleneimine for at least 1 hour) using a 40-well filtration manifold. Test compounds were added at appropriate concentrations (60 minutes incubation time), in such a way that the inhibition curves were defined by at least eight to twelve concentration points, measured in duplicate. All experiments were repeated independently at least two times. Radioactivity on the filters was counted in a Packard Tri-carb 1600CA liquid scintillation analyzer. Counting data were collected directly in a Macintosh SE personal computer and further transferred to a Macintosh II personal computer. Counting data from assays in the presence of a compound were automatically expressed as percent of total binding measured in the absence of test compound. Inhibition curves plotting percent of total binding versus the log concentrations of the test compound were automatically generated. The sigmoidal inhibition curves were analyzed by computerized curve-fitting, with a programme using non-linear regression analysis for one- or two site curve fitting (modifications of equations described in Oestreicher E. G. and Pinto G. F., *Comput. Biol. Med.,* 17, 53–68 (1987). The log $IC_{50}$ values ($pIC_{50}$; $IC_{50}$ defined as the concentration producing 50% inhibition of specific radioligand binding) were derived from individual curves. $K_i$ values were calculated according to the method of Cheng and Prusoff (Cheng Y. C. and Prusoff W. H., *Biochem. Pharmacol.,* 22, 3099–3108, 1973)$[K_i=IC_{50}/(1+C/K_D)]$ using the $K_D$ (1.7 nM) and the concentration (C) of the radiolabelled $[^3H]$GR 65630 (2 nM). The $K_i$ values of the test compounds are presented as logarithmic mean and corresponding 95% confidence limits of the various determinations; and are presented in Table 1 in the column labelled "$5HT_3$ receptor $K_i$(95% c.l.) nM".

Study 1: $MgSO_4$ Induced Intestinal Lavage

Beagle dogs (of both sexes and varying in body weight, 16 hours deprived from food) were orally pretreated with the test compound (0.5 ml/kg) and challenged 1 hour later with an oral administration of magnesium sulphate ($MgSO_4.7H_2O$, 64 g/l, 0.26 M; 200 ml). The onset of $MgSO_4$-induced intestinal lavage was assessed over a period of 4 hours after challenge. Liquid stools within 4 hours occured almost never in control animals treated with distilled water (3.0% false positives; n>100) and were considered to reflect significant acceleration of the $MgSO_4$-induced intestinal lavage. Doses in the active dose range were given to five animals each, tested in separate experimental sessions including solvent-treated control animals. All-or-none criteria, based on the distribution of the results obtained in a large number of solvent-treated animals, were used to calculate $ED_{50}$-values and 95% confidence limits (c.l.) according to Finney's iterative method (Finney D. J., "*Probit analysis*", Cambridge University Press, 1962).

Test Compounds

The following test compounds were obtained from the companies of origin: bemesetron, BIMU-8, DAU-6236, granisetron, ondansetron, tropisetron, YM-060, renzapride and zacopride, as well as Compound A.

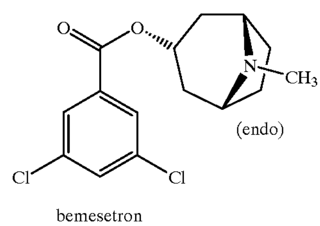

bemesetron

-continued

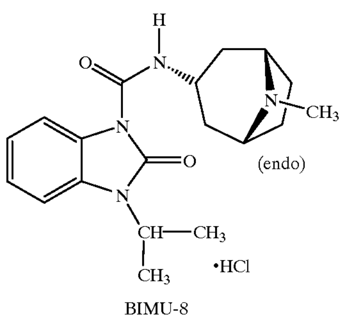

BIMU-8

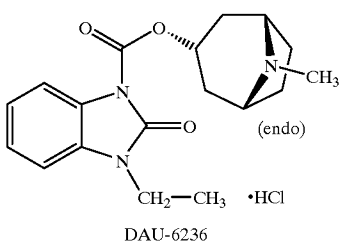

DAU-6236

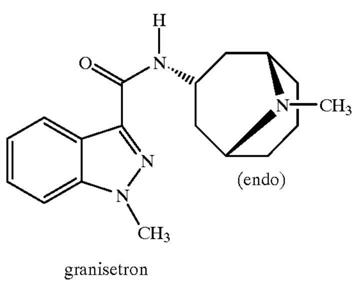

granisetron

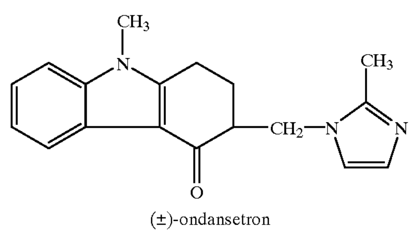

(±)-ondansetron

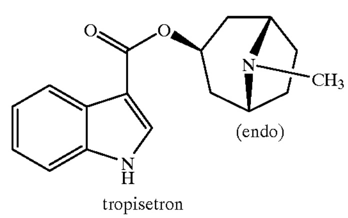

tropisetron

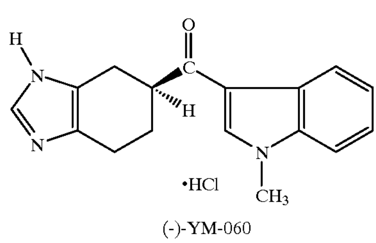

(-)-YM-060

-continued

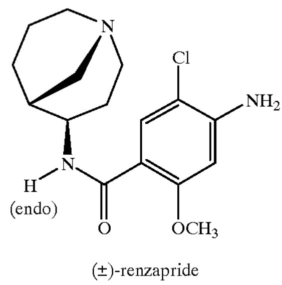

(±)-renzapride (+)-zacopride (-)-cis compound A

Results

The active doses or concentrations of the test compounds have been listed in Table 1. All compounds showed affinity for the $5HT_3$ receptor, inhibited 5-hydroxykynuramine (5-OH-K)-induced contractions of the guinea-pig ileum, antagonized the Von Bezold Jarisch reflex and stimulated gastric emptying in rats, and the accelerated appearance of $MgSO_4$-induced loose stools in dogs.

TABLE 1

Binding to the serotonin $5HT_3$ receptor ($K_i$, nM); and acceleration of $MgSO_4$ induced diarrhea in dogs ($ED_{50}$, μg/kg, po).

| | Test compound | $5HT_3$ receptor $K_i$ (95% c.l.) nM | $MgSO_4$ induced intestinal lavage $ED_{50}$ (95% c.l.) μg/kg, po |
|---|---|---|---|
| 1 | (−)-YM-060 | 0.14 (0.050–0.36) | 1.2 (0.73–1.9) |
| 2 | BIMU-8 | 0.29 (0.12–0.70) | 16 (11–24) |
| 3 | (±)-Zacopride | 0.46 (0.34–0.62) | 23 (16–35) |
| 4 | (endo)-Tropisetron | 0.78 (0.35–1.7) | 74 (55–100) |
| 5 | (endo)-Granisetron | 2.6 (1.2–5.7) | 14 (10–19) |
| 6 | DAU-6236 | 6.6 (3.2–14) | 49 (36–67) |
| 7 | Bemesetron | 8.0 (2.2–29) | 770 (480–1250) |
| 8 | (±)-Ondansetron | 8.4 (6.2–11) | 97 (72–130) |
| 9 | (±)-Renzapride | 10. (4.4–23) | 74 (46–120) |
| 10 | Compound A | 0.58 (0.10–3.4) | 2.7 (1.8–4.0) |

Study 2: KleanPrep®-Induced Intestinal Lavage

The dogs were orally pretreated with test compound or distilled water (0.5 ml/kg) and 1 hour later challenged by gavage with KleanPrep® solution. Dependent on the type of experiment, the KleanPrep® solution was administered more than once at 15 minutes intervals. The standard administration volume was 200 ml. The occurrence of liquid stools at 1, 2, 3, 4, 5 and 6 hours after the first administration of KleanPrep® was noted. The KleanPrep® solution consisted of polyethyleneglycol 3350 (59 g/l), sodium sulfate (5.685 g/l), sodium hydrogencarbonate (1.685 g/l), sodium chloride (1.465 g/l), potassium chloride (0.7425 g/l), aspartate (0.0494 g/l) and vanille (0.3291 g/l).

Each dose of the test compounds was given to 5 animals. All-or-none criteria were used to calculate $ED_{50}$-values and 95% confidence limits according to the iterative method of Finney (Finney, D. J., *"Probit analysis"*, Cambridge University Press, 1962).

In a first experiment, five dogs were treated at 15 minutes intervals with 200 ml KleanPrep® until the occurrence of the first liquid stool. During the process of KleanPrep® administration, the abdomen of the dogs gradually distended as a consequence of the steadily increasing administered volume of KleanPrep® and the dogs started to urinate. Two dogs produced the first liquid stool after the 7th administration of KleanPrep® (corresponding to a total volume of 1400 ml; the first liquid stool at 95 and 101 min). A third dog displayed the first liquid stool after 9 administrations (1800 ml KleanPrep®; the first liquid stool at 124 min). The other two dogs vomited just after the 14th KleanPrep® administration (as much as 2800 ml KleanPrep®), after which further administration was stopped; they displayed the first liquid stool at 211 and 305 minutes after the start of the KleanPrep® administration.

In a second experiment, the occurrence of liquid stools was determined at several time intervals after single administration of 200 ml KleanPrep® in dogs pretreated one hour earlier with water (0.5 ml/kg, p.o.) or "COMPOUND A" (0.16 mg/kg, p.o.). None of the five dogs pretreated with water displayed liquid stools during a 4 hour observation period starting after the KleanPrep® administration. In contrast, three out of five dogs treated with "COMPOUND A" displayed liquid stools within 2 hours after KleanPrep® administration.

In a third experiment, the occurrence of liquid stools was determined at several time intervals after four administrations of KleanPrep® (4×200 ml at 15 minute intervals) in dogs pretreated one hour earlier with water (0.5 ml/kg, p.o.) or "COMPOUND A" (0.16 mg/kg, p.o.). Even at the end of the 6 hour observation period, only one out of five dogs pretreated with water had produced liquid stools (onset at 255 minutes after the first administration of KleanPrep®. On the other hand, all five dogs pretreated with "COMPOUND A" displayed their first liquid stool within 2 hours (at 38, 39, 42, 52, and 77 minutes) after the first administration of KleanPrep®.

In a fourth experiment, the occurrence of liquid stools was determined at several time intervals after two administrations of KleanPrep® (2×200 ml) in dogs pretreated one hour earlier with water (0.5 ml/kg, p.o.) or several doses of "COMPOUND A". In twenty five controls animals pretreated with water (0.5 ml/kg, p.o.), liquid stools remained absent up to 6 hours after the first administration of KleanPrep®. After oral pretreatment with "COMPOUND A", however, liquid stools were already observed within 4 hours ($ED_{50}$: 0.0036 mg/kg). Higher doses of "COMPOUND A" were able to further accelerate the occurrence of liquid stools to within 3 hours (dose increment: 1.1 times), 2 hours (dose increment: 3 times), and even 1 hour after KleanPrep® (dose increment: 24 times; $ED_{50}$: 0.085 mg/kg). According to the responsible technician, furthermore, it was conspicuous that urination was observed in all control animals but never in animals pretreated with effective doses of "COMPOUND A".

The present results confirm that "COMPOUND A" and other $5HT_3$ antagonists as well act synergistically with orally administered osmotic agents to induce liquid stools in dogs.

What is claimed is:

1. A product comprising a $5HT_3$ antagonist and an osmotic agent for simultaneous, separate or sequential use in the treatment of constipation or for accelerating intestinal lavage, provided that said product does not contain an opiod antagonist, wherein the osmotic agent is a polyethylene glycol (PEG)-electrolyte solution.

2. The product according to claim 1, wherein the $5HT_3$ antagonist is selected from the group consisting of Azasetron, Granisetron, Ondansetron, Torpisetron, DAT-582, Dolasetron, Itasetron, N-3389, Pancopride, Ramosetron, RG-12915, (R)-Zacopride, Lurosetron, E-3620, GK-128, KB-6933, KF-20170, SL-90.0539 and (−)-cis-4-amino-5-chlor-2,3-dihydro-N-[1-[3-[(3,4-dihydro4-oxo-2-pyrimidinyl)amino]-propyl]-3-methoxy-4-piperidinyl]-2,2-dimethyl-7-benzofurancarboxamide and the pharmaceutically acceptable acid addition salts thereof.

3. The product according to claim 1, wherein the polyethylene glycol (PEG)-electrolyte solution and the $5HT_3$ antagonist are each administered in separate oral dosage forms.

4. The product according to claim 1, wherein the polyethylene glycol (PEG)-electrolyte solution and the $5HT_3$ antagonist are administered together in a combination oral dosage form.

* * * * *